(12) United States Patent
Nunome et al.

(10) Patent No.: US 8,715,198 B2
(45) Date of Patent: May 6, 2014

(54) SPHYGMOMANOMETER EXHAUST VALVE AND SPHYGMOMANOMETER USING THE SAME

(75) Inventors: Tomohiro Nunome, Komaki (JP); Takehito Fukunaga, Kasugai (JP)

(73) Assignee: Fukuda Denshi Co., Ltd., Tokyo (JP)

( * ) Notice: Subject to any disclaimer, the term of this patent is extended or adjusted under 35 U.S.C. 154(b) by 1470 days.

(21) Appl. No.: 11/808,065

(22) Filed: Jun. 6, 2007

(65) Prior Publication Data

US 2007/0287926 A1    Dec. 13, 2007

(30) Foreign Application Priority Data

Jun. 7, 2006  (JP) .................................. 2006-159107

(51) Int. Cl.
*A61B 5/02*     (2006.01)
*F16K 31/02*    (2006.01)
*F16K 1/16*     (2006.01)

(52) U.S. Cl.
USPC .......................... 600/498; 251/129.2; 251/298

(58) Field of Classification Search
USPC ........ 600/485, 490, 495, 498; 251/129.2, 298
See application file for complete search history.

(56) References Cited

U.S. PATENT DOCUMENTS

| 3,603,559 | A | * | 9/1971 | Totten ........................ 251/129.2 |
| 4,250,924 | A | * | 2/1981 | Sakakibara et al. .......... 137/868 |
| 4,268,009 | A | * | 5/1981 | Allen, Jr. .................... 251/129.2 |
| 4,500,069 | A | * | 2/1985 | Barber et al. ................. 251/282 |
| 4,545,563 | A | * | 10/1985 | Morioka et al. ............. 251/298 |
| 4,721,438 | A | * | 1/1988 | Ichinomiya et al. .......... 417/316 |
| 5,156,184 | A | * | 10/1992 | Kolchinsky ................ 137/454.5 |
| 5,370,029 | A | * | 12/1994 | Kramer ........................... 84/339 |
| 5,556,073 | A | * | 9/1996 | Wawro et al. ............. 251/129.11 |
| 6,453,936 | B1 | * | 9/2002 | Frank et al. .............. 137/315.03 |
| 2007/0069167 | A1 | * | 3/2007 | Stark et al. ................. 251/129.2 |
| 2007/0239042 | A1 | * | 10/2007 | Takahashi ..................... 600/498 |

FOREIGN PATENT DOCUMENTS

| JP | Y-56-41687   | 9/1981 |
| JP | 59-141934    | 8/1984 |
| JP | 02-309926 A  | 12/1990 |

* cited by examiner

*Primary Examiner* — Navin Natnithithadha
*Assistant Examiner* — Michael R Bloch
(74) *Attorney, Agent, or Firm* — Drinker Biddle & Reath LLP

(57) ABSTRACT

Disclosed is a sphygmomanometer exhaust valve having a valve that functions as a lever, and in which a solenoid moves the point of force of the valve to urge a valve membrane formed at the point of action against a ventilation port. A support member supports the valve while fixing its fulcrum. When no electric current is supplied to the solenoid, the support member holds the valve in a predetermined position in which the ventilation port is open.

4 Claims, 8 Drawing Sheets

SPHYGMOMANOMETER EXHAUST VALVE AND SPHYGMOMANOMETER USING THE SAME

CLAIM OF PRIORITY

This application claims priority from Japanese Patent Application No. 2006-159107, filed on Jun. 7, 2006, which is hereby incorporated by reference herein.

BACKGROUND OF THE INVENTION

1. Field of the Invention

The present invention relates to an exhaust valve suitably usable in a sphygmomanometer and a sphygmomanometer using the same.

2. Description of the Related Art

Blood pressure is extensively used as a value reflecting the state of circulatory organs, and various sphygmomanometers have been developed. Although blood pressure is measured on the basis of various principles, sphygmomanometers using a so-called oscillometric method is widely used.

The oscillometric method avascularizes a measurement portion such as an extremity by externally pressing it, detects oscillations from the blood vessel (artery) while gradually lowering the pressure, and measures the blood pressure on the basis of the oscillations and pressure.

A sphygmomanometer based on the oscillometric method generally presses a measurement portion by using a cuff. To increase the pressure of the cuff, the sphygmomanometer supplies a gas such as air to an air bag inside the cuff. To reduce the pressure, the sphygmomanometer exhausts the gas from the air bag by opening an exhaust valve.

As described above, when a sphygmomanometer of this type is used, the pressure must be gradually lowered from the avascularized state. It is important to maintain the exhaust rate (exhaust flow rate) ideally constant, and, in practice, within a predetermined range centering around a target value.

For this purpose, reference 1 (Japanese Utility Model Publication No. 56-41687) has proposed an exhaust device having an exhaust nozzle extending through the core of a solenoid, and a valve membrane that opens and closes by the operation of the solenoid. This exhaust device adjusts the exhaust amount by an electric current supplied to the solenoid.

Also, reference 2 (Japanese Patent Laid-Open No. 59-141934) has proposed an arrangement in which in an exhaust amount control valve uses a solenoid positioned so as to be cooled by the exhaust gas, in order to suppress the influence which the heat generated by an electromagnet in the solenoid has on the physical properties and flow rate of the valve.

In the arrangement described in reference 1, however, the exhaust nozzle extends through the core of the solenoid. This inevitably increases the size of the solenoid. Also, the structure is not hermetically sealed even while the valve membrane is pushed against the nozzle opening by supplying an electric current to the solenoid. This makes it difficult to stably adjust particularly the initial flow rate.

The structure described in reference 2 cools the solenoid by using the exhaust gas. Therefore, the solenoid is positioned such that its longitudinal direction is perpendicular to the exhaust channel. This complicates the mechanism that opens and closes the valve.

SUMMARY OF THE INVENTION

The present invention has been made in consideration of the problems of the prior art as described above, and provides a sphygmomanometer exhaust valve capable of accurately adjusting the exhaust flow rate using a simple arrangement.

According to an aspect of the present invention, there is provided a sphygmomanometer exhaust valve characterized by comprising: a movable member which functions as a lever; a ventilation port formed in a position opposing a first portion which functions as a point of action of said movable member; control unit adapted to control, in accordance with external control, an amount of movement of a second portion which functions as a point of force of said movable member; and support unit adapted to support a fulcrum of said movable member, wherein said support unit supports said movable member such that a fulcrum position of said movable member does not move, and, while said control unit is preventing movement of the point of force of said movable member, holds said movable member in a predetermined position where the point of action of said movable member is spaced apart from said ventilation port.

The sphygmomanometer exhaust valve of the present invention can accurately adjust the exhaust flow rate using a simple arrangement as described above.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Preferred embodiments of the present invention will now be described in detail in accordance with the accompanying drawings.

Figure 1:
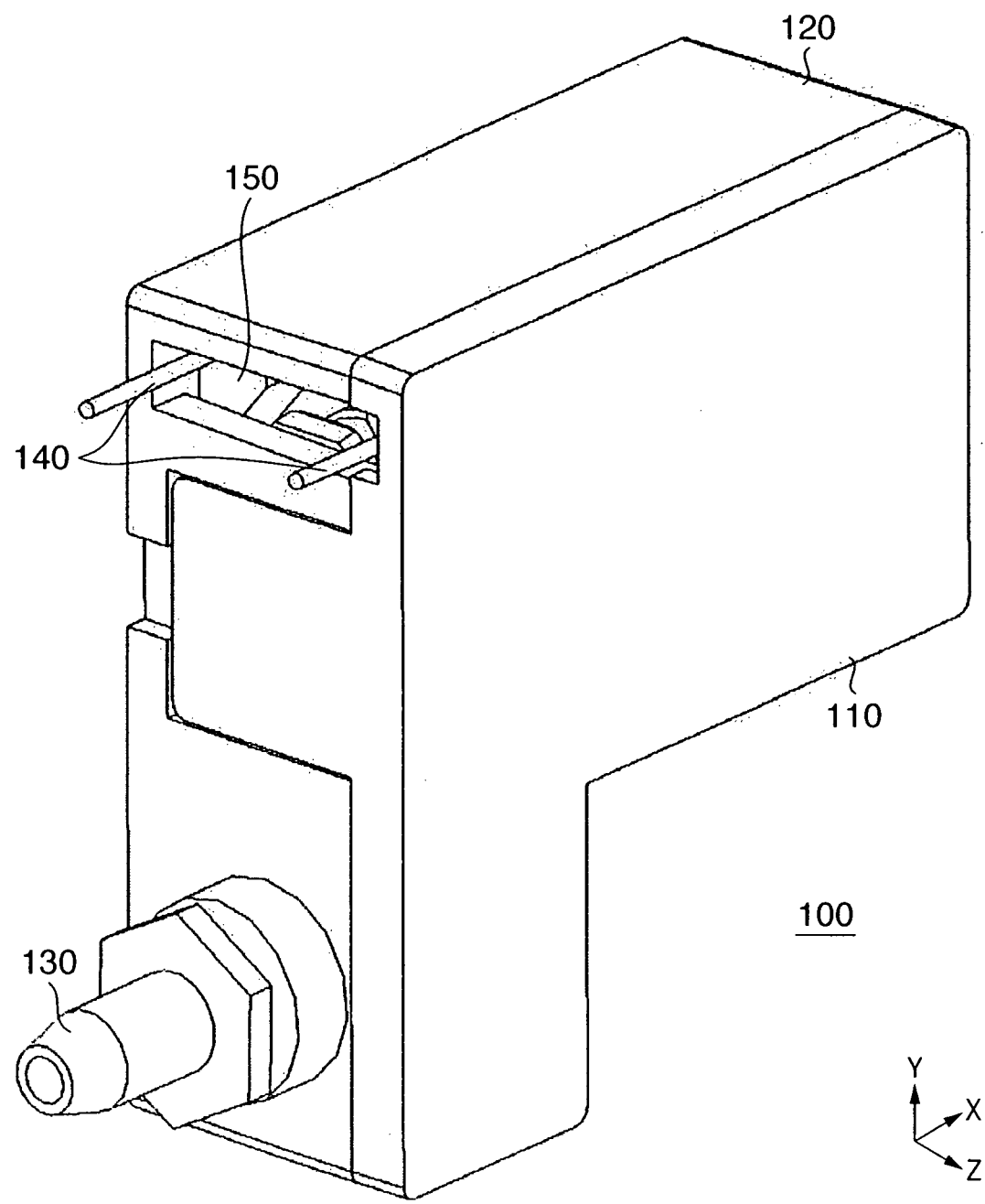
FIG. 1 is a perspective view showing an example of the outer appearance of a sphygmomanometer exhaust valve 100 according to an embodiment of the present invention.

FIG. 1 is a perspective view showing an example of the outer appearance of a sphygmomanometer exhaust valve 100 according to an embodiment of the present invention.

Referring to FIG. 1, the sphygmomanometer exhaust valve 100 has a hollow casing made up of an upper case 110 and lower case 120. A connector 130 is connected to the air bag of a cuff (not shown), for example, by a hose or tube. A lead 140 is connected to a driving power supply (not shown). An opening 150 functions as an exhaust hole.

Figure 2:
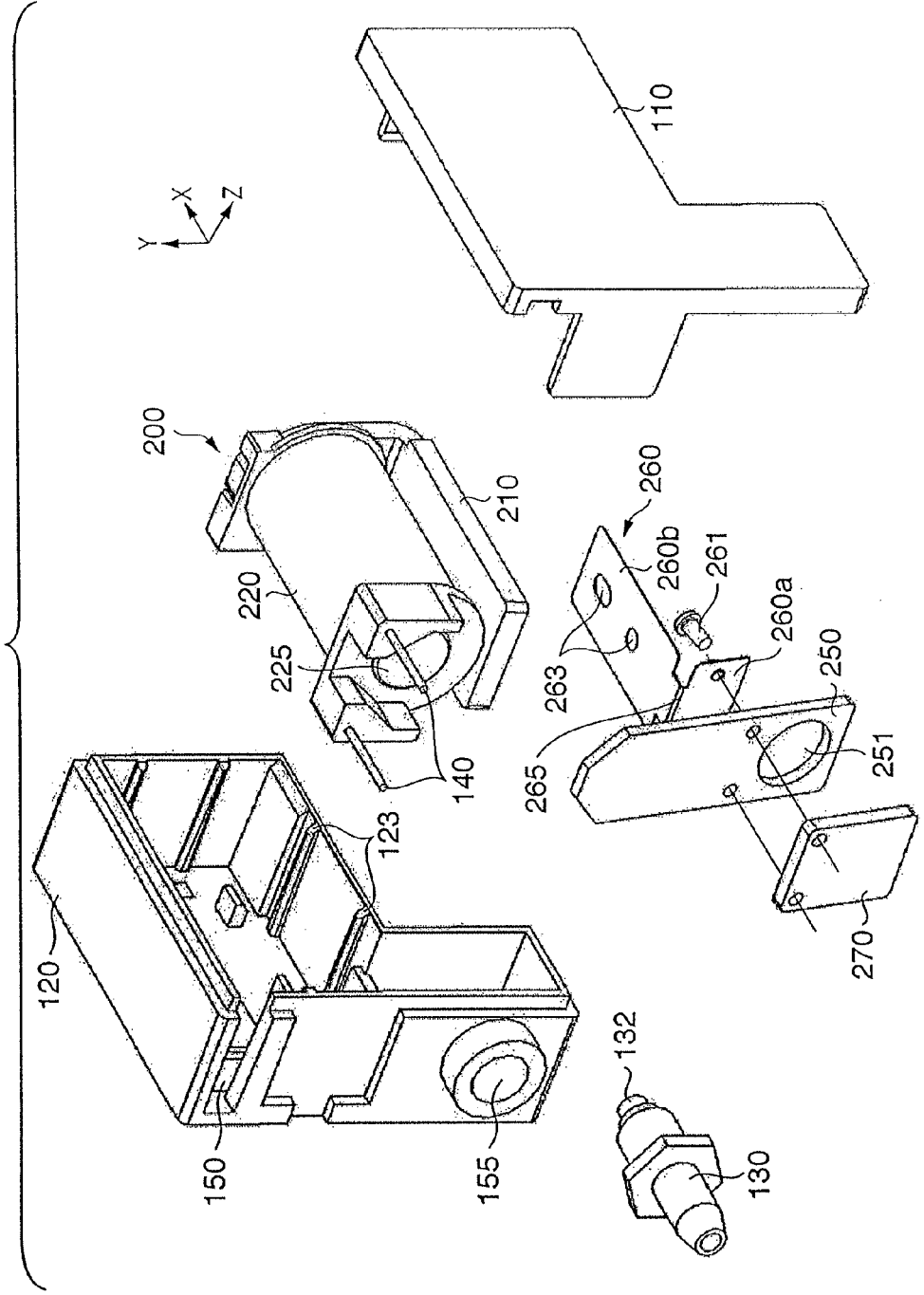
FIG. 2 is an exploded perspective view showing the arrangement of the sphygmomanometer exhaust valve 100 shown in FIG. 1 in more detail.

FIG. 2 is an exploded perspective view showing the arrangement of the sphygmomanometer exhaust valve 100 in more detail.

In this embodiment, the sphygmomanometer exhaust valve 100 uses an attraction type solenoid 200 as a means for controlling the valve opening ratio, and can adjust the exhaust flow rate by controlling an electric current supplied to the solenoid 200. The solenoid 200 is an electromagnet that has a coil 220, yoke 210, and core 225, and changes its attracting force in accordance with the value of an externally supplied electric current.

A valve 250 as an example of a movable member that functions as a lever is a generally rectangular plate-like member made, for example, of iron. A valve membrane 270 made of a flexible material such as silicone rubber is formed on the surface of one end portion that functions as the point of action of the valve 250. Also, a hole 251 for allowing easy deformation of the valve membrane 270 is formed in one end portion of the valve 250. The other end portion, which functions as the point of force of the valve 250, is placed in a position opposing the core 225 of the solenoid 200. Accordingly, the solenoid 200 functions as a means for controlling the amount of movement of the point-of-force of the valve 250.

Note that the material and arrangement of the valve 250 are not limited as long as the valve 250 is attracted by the magnetic force generated by the solenoid 200 and has at least enough rigidity to such that the attracting force of the solenoid 200 allows the valve membrane 270 to hermetically seal a ventilation port 134 of a terminal portion 132 of the connector 130.

In this embodiment, a support member 260 is fastened to the valve 250 by screws 261. The support member 260 of this embodiment is a thin plate-like member having spring properties, and bent into an L-shape in a bent portion 265. The valve 250 is attached to a first portion 260a so that the bent portion 265 functions as the fulcrum of the valve 250 as a lever. A second portion 260b of the support member 260 is sandwiched and fixed between the bottom surface of the yoke 210 of the solenoid 200 and the lower case 120, in order to fix the bent portion 265.

The connector 130 is fitted in a fitting portion 155 of the lower case 120. The terminal portion 132 of the connector 130 protrudes into the lower case 120 to connect the inner space of the case and the inner space of the air bag by the ventilation port 134 and a hose connected to the connector 130.

Figure 3:
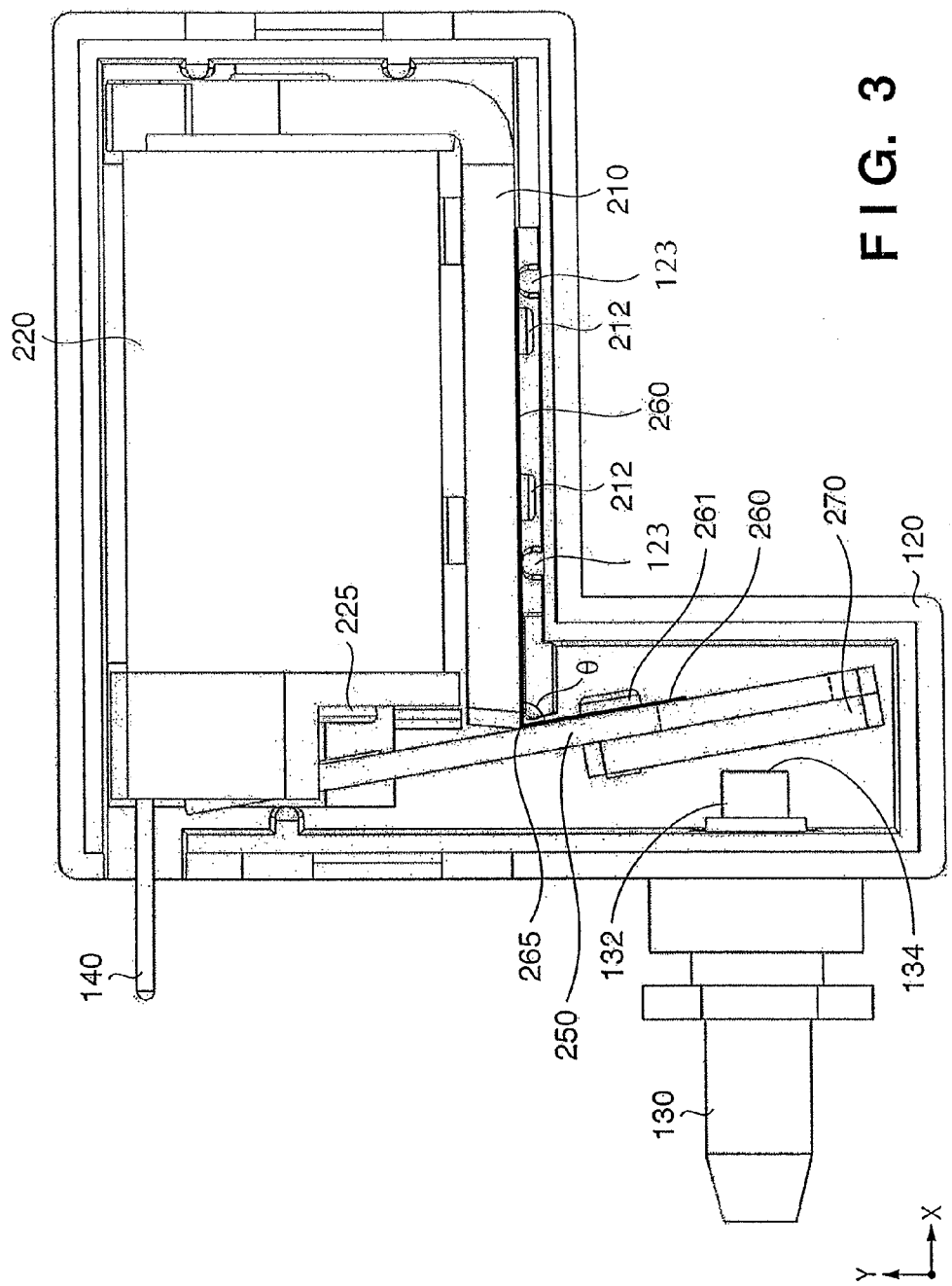
FIG. 3 is a side view showing the state in which an upper case 110 is removed from the sphygmomanometer exhaust valve 100 in an assembled state.

FIG. 3 is a side view showing the state in which the upper case 110 is removed from the sphygmomanometer exhaust valve 100 in an assembled state. FIG. 3 shows the state in which no electric current is supplied to the solenoid 200.

When assembling the valve, a projection 212 formed on the bottom surface of the yoke 210 is fitted in a hole 263 formed in the second portion 260b of the support member 260, thereby attaching the solenoid 200 to the lower case 120. In this manner, ribs 123 formed on the lower case inner surface and the yoke 210 sandwich and fix the second portion 260b of the support member 260.

The length of the second portion 260b of the support member 260 is determined such that the bent portion 265 of the support member 260 almost aligns with the distal end portion of the yoke 210 of the solenoid 200. A bending angle θ of the support member 260 is the angle between the plane formed by the first portion 260a to which the valve 250 is fastened and the plane formed by the second portion 260b sandwiched between the yoke 210 and the ribs 123 of the lower case 120. The value of the bending angle θ is determined such that the valve 250 fully opens; in other words, the valve membrane 270 formed at one end portion of the valve 250 completely opens the ventilation port 134 of the terminal portion 132 when no electric current is supplied to the solenoid 200, and the attracting force generated by the solenoid 200 can fully close the valve 250; thus the valve membrane 270 can hermetically seal the ventilation port 134. The bending angle θ can be appropriately determined by the rigidity and length of the valve 250, the performance of the solenoid 200, and the like.

In the arrangement of this embodiment as shown in FIG. 3, the support member 260 and valve 250 are connected so as to position the bent portion 265 of the support member 260 near the center of the valve 250. Since the second portion 260b of the support member 260 is fixed, the movement of the valve 250 is limited to the rotation around the bent portion 265 of the support member 260. The valve 250 thus functions as a lever having the bent portion 265 as the fulcrum, one end portion as the point of action, and the other end portion as the point of force.

When an electric current is supplied to the solenoid 200 and the solenoid 200 generates an attracting force, the other end portion of the valve 250 comes close to the core 225, and one end portion of the valve 250 comes close to the terminal portion 132 positioned on the side of the valve 250 away from the core 225. When the attracting force increases, the valve membrane 270 at one end portion comes in contact with the terminal portion 132 of the connector 130, and gradually closes the ventilation port 134 of the terminal portion 132.

The support member 260 is made, for example, of a thin steel plate, and has elastic properties. The valve 250 is held by setting the bending angle θ described above such that when no electric current is supplied to the solenoid 200, the valve membrane 270 is in a predetermined position apart from the terminal portion 132 of the connector 130.

Since the support member 260 is fixed, the fulcrum (bent portion 265) does not move while the valve 250 is moving even when it is used in an orientation in which the connector 130 vertically faces down. Also, the rigidity of the support member 260 holds the distance between the valve membrane 270 and terminal portion 132 generally constant in the full open position shown in FIG. 3.

Accordingly, the posture in operation of the sphygmomanometer exhaust valve 100 of this embodiment is not limited. This increases the degree of freedom of design of the sphygmomanometer, and makes it unnecessary to measure the blood pressure by maintaining the sphygmomanometer in a specific posture. It should be clear that the force with which the support member 260 holds the position of the valve 250 need only have power that is much smaller than the maximum attracting force generated by the solenoid 200, and allows the valve 250 to return to a predetermined position even if an external force such as gravity or a vibration is applied to it.

The arrangement described in reference 1 or 2 mentioned earlier has neither a mechanism to fix the rotating shaft of the valve, nor a mechanism to hold the position of the valve when no electric current is supplied to the solenoid. Therefore, when gravity or a vibration moves the whole valve and turns it upside down, the valve membrane comes in contact with the connector hole. Therefore, when the exhaust device or control valve described in reference 1 or 2 is applied into a sphygmomanometer, the orientation of the sphygmomanometer is restricted at least while it is in use.

Figure 4:
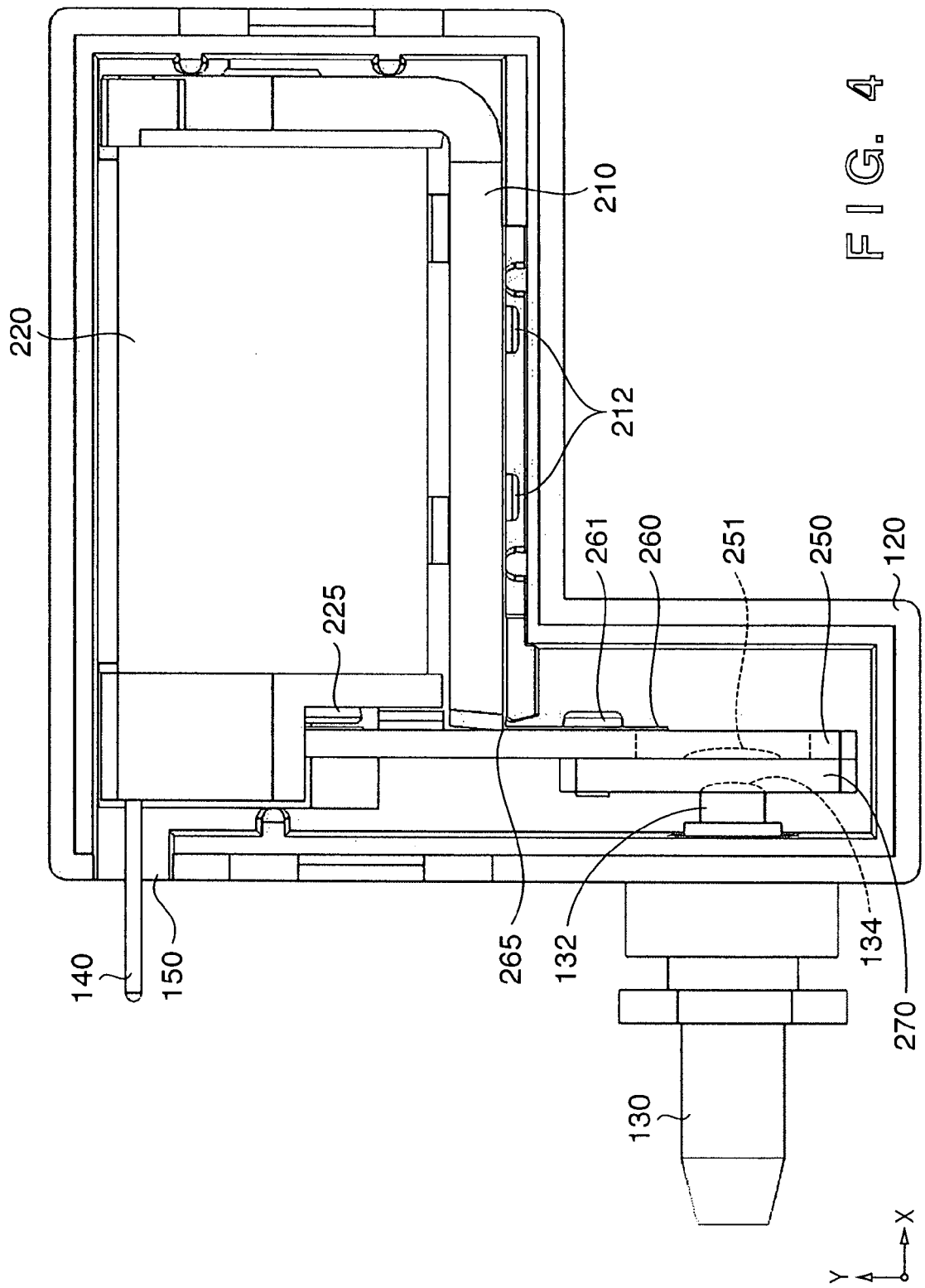
FIG. 4 is a side view showing the state in which the upper case 110 is removed from the sphygmomanometer exhaust valve 100 in the assembled state.

FIG. 4 is a side view showing the state in which an electric current is supplied to the solenoid 200 from the state shown in FIG. 3, and the core 225 has completely attracted the other end portion of the valve 250. That is, the sphygmomanometer exhaust valve 100 is fully closed when viewed from the sphygmomanometer.

In this full closed state, an electric current is supplied to the solenoid 200 so as to generate an attracting force sufficient to allow the valve membrane 270 to completely seal the ventilation port 134 in the terminal portion 132 of the connector 130. In this state, the hole 251 formed in one end portion of the valve 250 helps the valve membrane 270 deform in accordance with the shape of the terminal portion 132, thereby achieving sufficient hermetic sealing properties (airtightness). Referring to FIG. 4, the dotted lines indicate the state in which the valve membrane 270 deforms by the urging force (the attracting force of the solenoid 200).

As described above, when an electric current is supplied to the solenoid 200 from a controller (not shown) through the lead 140, the coil 220 generates a magnetic force, and the core 225 generates a force that attracts the valve 250. This attracting force increases as the amount of electric current supplied to the solenoid 200 increases. Accordingly, it is possible to achieve an arbitrary valve opening ratio from the full open state to the full closed state by appropriately controlling the amount of electric current.

In addition, as will be described later, while a pressure sensor is sensing the internal pressure (to be also referred to as the cuff pressure hereinafter) of the air bag, if the pressure reduction ratio per unit time is higher than a target value, the exhaust flow rate is decreased by increasing the amount of electric current supplied to the solenoid 200, and, if the pressure reduction ratio is lower than the target value, the exhaust flow rate is increased by decreasing the amount of electric current supplied to the solenoid 200. The cuff pressure can be stably reduced by thus performing feedback control.

It is also possible to perform similar control by using the difference between an actual measurement value and a target internal pressure value calculated from the internal pressure of the air bag at the start of pressure reduction and the target pressure reduction ratio.

In this embodiment as described above, in the sphygmomanometer exhaust valve that uses the movable member functioning as a lever, and adjusts the exhaust flow rate by controlling the amount of rotation (the amount of movement of the point of force) of this movable member, the support member supporting the fulcrum of the movable member is fixed, the position of the valve when the amount of rotation is not controlled is maintained to be nearly constant. This makes it possible suppress the influence of an external force such as gravity or a vibration on the valve position.

This reduces variations in actual amount of rotation with respect to the amount-of-rotation control value, and makes stable flow rate control feasible particularly in the initial state. For example, when controlling the amount of rotation by using the attracting force generated by the solenoid, control can be performed with high reproducibility by previously obtaining the relationship between the target exhaust flow rate value and the amount of electric current supplied to the solenoid.

Note that this embodiment uses the support member 260 formed by bending a thin plate-like member. However, the support member 260 can have any form as long as it fixes the fulcrum (rotational axis) of the valve 250, and can maintain the position of the valve 250 to be nearly constant in the full open position when no electric current is supplied to the solenoid 200.

For example, the support member 260 may also have the form of a hinge obtained by connecting the first and second portions 260a and 260b as individual members by a common shaft. In this case, when no electric current is supplied to the solenoid 200, the valve position can be held by using a well-known arrangement, for example, by biasing the valve in the direction of decreasing the bending angle θ using a spring attached to the shaft, and limiting the motion of the hinge using a stopper or the like so as not to excessively decrease the bending angle θ.

Figure 5A:
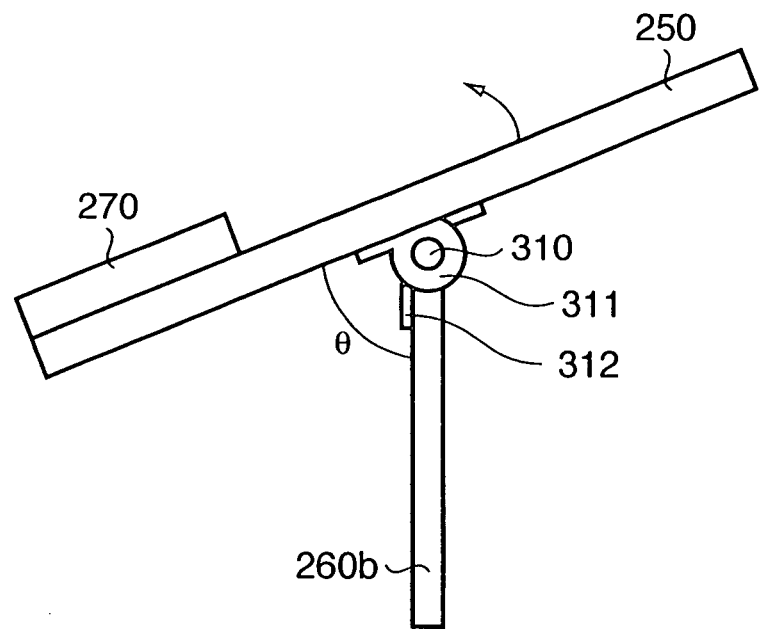
FIGS. 5A and 5B are views showing another example of the arrangement of the sphygmomanometer exhaust valve according to the embodiment of the present invention.
Figure 5B:
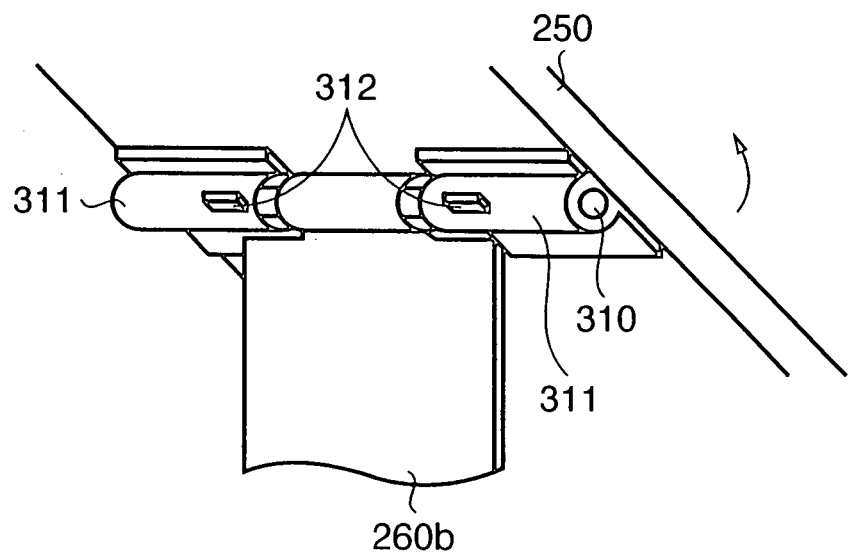

FIGS. 5A and 5B illustrate still another arrangement. As shown in FIGS. 5A and 5B, it is also possible to directly attach bearings 311 to the valve 250 without using the first portion 260a, and connect the second portion 260b so that it can pivot via a shaft 310. It is possible to attach a biasing spring (not shown) to the shaft 310 and form a stopper 312 to limit the minimum value of the angle θ obtained by the biasing force in this case as well. FIG. 5A is a schematic view showing the state in which no electric current is supplied to the solenoid 200. FIG. 5B is a schematic view showing the state in which an electric current is supplied to the solenoid 200.

Figure 6:
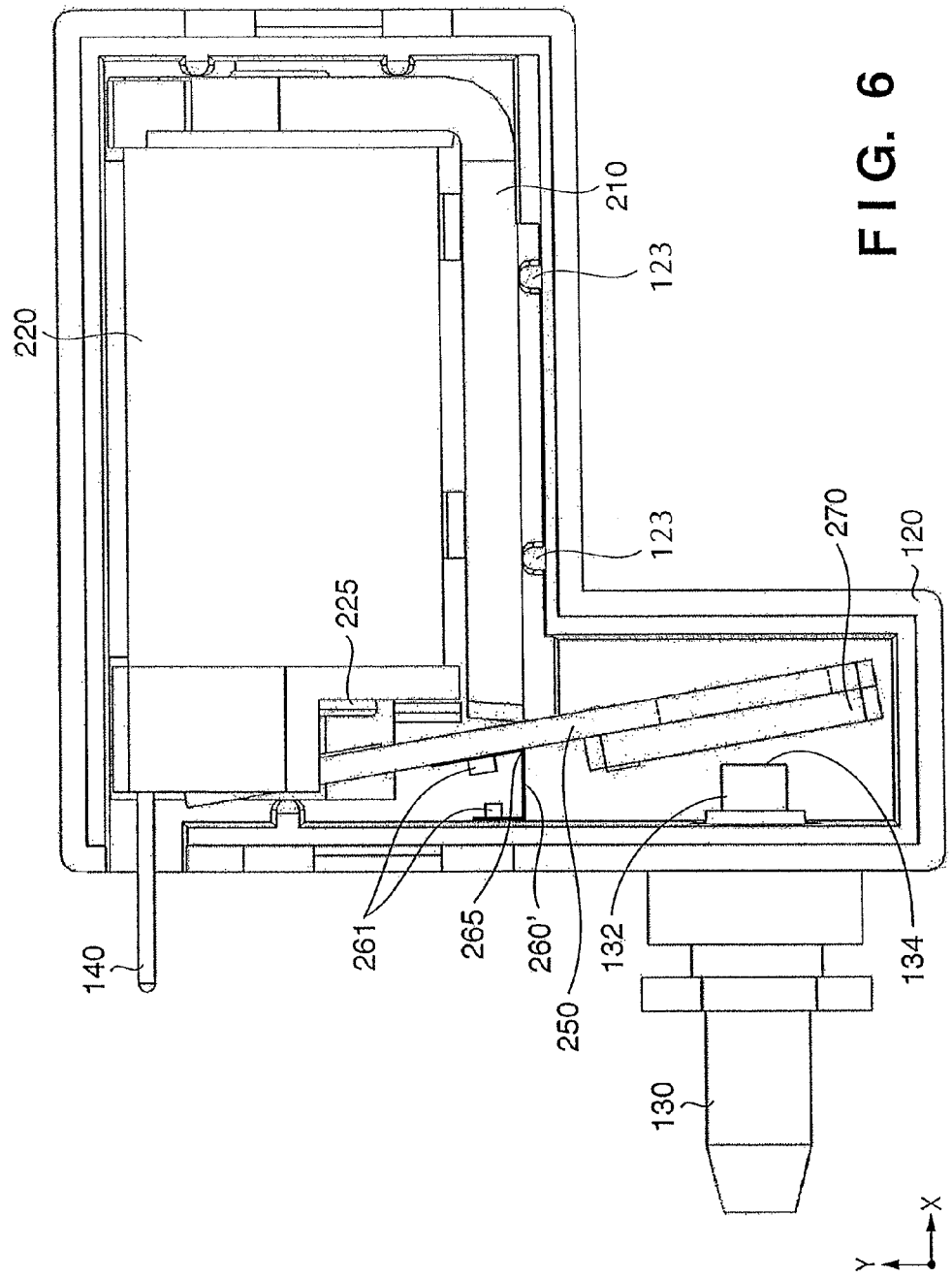
FIG. 6 is a view showing still another example of the arrangement of the sphygmomanometer exhaust valve according to the embodiment of the present invention.

In addition, the fulcrum of the valve 250 is fixed by connecting the support member 260 to the yoke 210 of the solenoid 200 in the above arrangement, but the support member 260 may also be connected to another portion. For example, as shown in FIG. 6, it is also possible to form a bent portion 265 functioning as the fulcrum on the surface on which the valve membrane 270 is formed, and connect an almost U-shaped support member 260' to the lower case 120.

Note that this embodiment has discussed an example using the almost rectangular plate-like valve. However, it should be clear that the valve 250 need not be a plate and can take any similar shape that functions as a lever. Accordingly, in this specification the term "plate" is used, however it may include many shapes such as a rod.

(Application to Sphygmomanometer)

Figure 7:
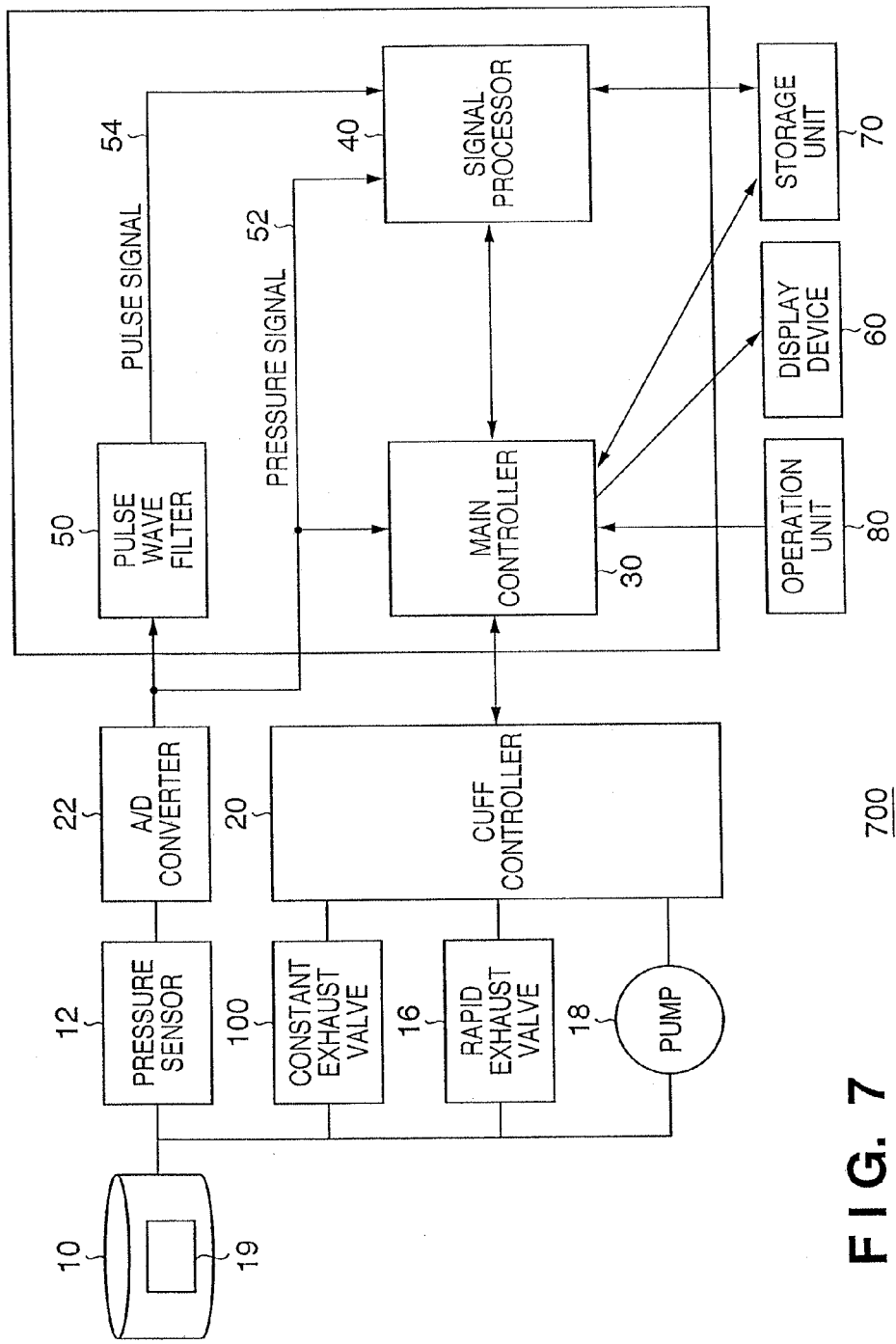
FIG. 7 is a block diagram showing an example of the arrangement of a sphygmomanometer using the sphygmomanometer exhaust valve 100 of this embodiment.

FIG. 7 is a block diagram showing an example of the arrangement of a sphygmomanometer using the sphygmomanometer exhaust valve 100 of this embodiment.

A cuff 10 of a sphygmomanometer 700 contains an air bag 19. When a pump 18 connected to the air bag 19 supplies air, the cuff 10 presses a portion of an object to be measured to which the cuff 10 is attached. Although the cuff 10 can be attached to any portion that can be avascularized, it is normally attached to one of the extremities. The air bag 19 is connected to the sphygmomanometer exhaust valve 100 described above as a constant exhaust valve (to be referred to as a constant exhaust valve 100 hereinafter). The air bag 19 is also connected to a rapid exhaust valve 16 as another exhaust valve. The rapid exhaust valve 16 need not have any flow control function, and need only be able to control two states: the full closed state and the full open state. When pressurizing the cuff, both the exhaust valves are fully closed. Under the control of a cuff controller 20, the constant exhaust valve 100 is opened when detecting a pulse wave during a time period from avascularization to determination of the blood pressure, and the rapid exhaust valve 16 is opened after the blood pressure is determined. The cuff controller 20 controls the pump 18, constant exhaust valve 100, and rapid exhaust valve 16 under the control of a main controller 30 (to be described later), thereby controlling the cuff pressure during measurement.

A pressure sensor 12 is connected to the air bag 19 of the cuff 10, in addition to the constant exhaust valve 100, rapid exhaust valve 16, and pump 18. The pressure sensor 12 is a pressure-electricity conversion sensor using, for example, a piezo-electric element, and outputs the internal pressure of the cuff (air bag 19) as an electrical signal. An A/D converter 22 samples this electrical signal (pressure signal) at a predetermined frequency, and converts the signal into digital data. The A/D converter 22 supplies a pressure signal 52 as the digital data to the main controller 30, a signal processor 40, and a pulse wave filter 50.

The pulse wave filter 50 extracts a pulse wave signal contained in the pressure signal. The pulse wave filter 50 can be implemented using a general bandpass filter that passes the frequency of a pulse wave. When an analog filter is used as the pulse wave filter 50, the output from the pressure sensor 12 is directly input to the pulse wave filter 50, and another A/D converter 22 is placed after the pulse wave filter 50.

The signal processor 40 receives a pulse signal 54 extracted by the pulse wave filter 50, and the pressure signal 52 output from the A/D converter 22. From the pressure signal 52 and pulse signal 54, the signal processor 40 performs a blood pressure determination process using a method based on the well-known oscillometric method, and determines minimum and maximum blood pressure values. The signal processor 40 notifies the main controller 30 of the determined blood pressure values.

The main controller 30 controls the operation of the whole sphygmomanometer 700, and achieves automatic blood pressure measurement. Note that FIG. 7 illustrates the main controller 30, signal processor 40, and pulse wave filter 50 as discrete units, but a single microprocessor (CPU) may also implement these units in the form of software by executing control software for implementing the functions of these units.

A display device 60 is, for example, a dot-matrix display such as an LCD or an LED lamp display. The display device 60 displays the operation state, measurement results, guidance, and the like of the sphygmomanometer 700 by using, for example, a graphical user interface (GUI) under the control of the main controller 30. Note that another output device such as a loudspeaker or printer may also be used instead of or in addition to the display device 60.

A storage unit 70 is a storage device that stores information necessary for the sphygmomanometer 700 to operate, information entered at the time of measurement (e.g., information of an object to be measured), measurement data, and the like. The storage unit 70 is, for example, a semiconductor memory or a magnetic recording device such as a hard disk drive. Note that when implementing the main controller 30, signal processor 40, pulse wave filter 50, and the like by software, control programs to be executed by the CPU are stored in the storage unit 70. The storage unit 70 is also used as a work area of the CPU.

Furthermore, the storage unit 70 may also be implemented by combining a plurality of types of storage devices such as a built-in memory and memory card reader.

An operation unit 80 is, for example, a unit having keys and buttons, or a touch panel attached to the display device 60. The user enters instructions to the sphygmomanometer 700 using the operation unit 80. The main controller 30 monitors the operation of the operation unit 80.

(Operation of Sphygmomanometer)

The cuff pressure control operation of the sphygmomanometer having the above arrangement will be explained below with reference to a flowchart shown in FIG. 8.

Figure 8:
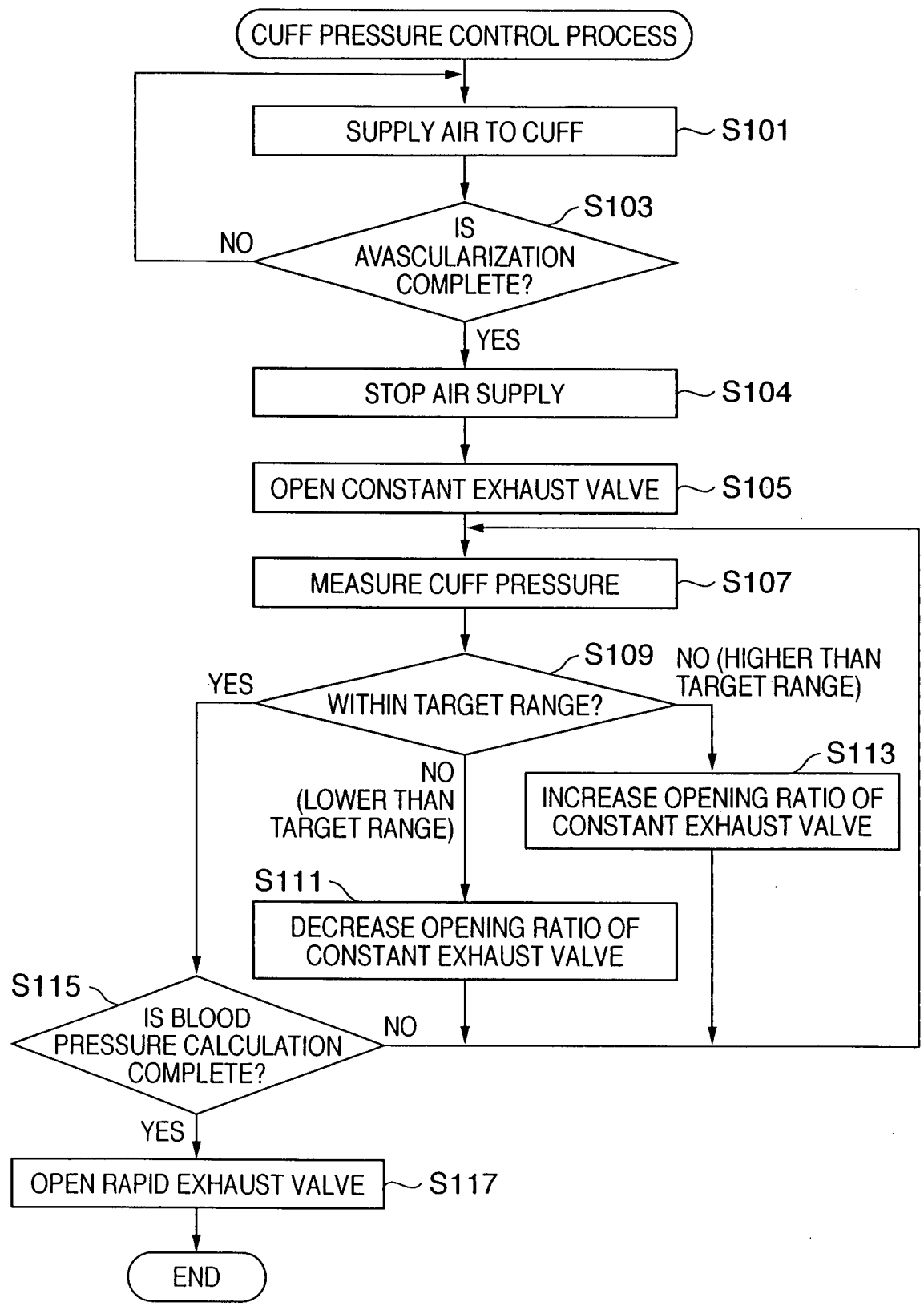
FIG. 8 is a flowchart for explaining a cuff pressure control process performed by the sphygmomanometer shown in FIG. 7.

FIG. 8 is a flowchart for explaining the cuff pressure control process of the sphygmomanometer of this embodiment.

When the user designates the start of a blood pressure measuring operation by pressing, for example, a start button of the operation unit 80, the main controller 30 instructs the cuff controller 20 to supply air to the cuff.

In response to this instruction, the cuff controller 20 starts supplying air to the air bag 19 by operating the pump 18 (S101). Note that in this state, the cuff controller 20 fully closes both the constant exhaust valve 100 and rapid exhaust valve 16. Accordingly, an electric current is supplied to the solenoid 200 of the constant exhaust valve 100 through the lead 14, and the core 225 attracts the valve 250 as shown in FIG. 4. The pressure of the cuff 10 is successively supplied as the pressure signal 52 to the main controller 30 and signal processor 40 via the pressure sensor 12 and A/D converter 22.

The main controller 30 monitors the pressure of the cuff 10 (S103). If the main controller 30 detects that the pressure of the cuff 10 has reached a predetermined target pressure (avascularization pressure), the main controller 30 instructs the cuff controller 20 to stop the air supply (S104). Alternatively, if the signal processor 40 confirms the disappearance of the pulse signal 54 in step S103, the signal processor 40 notifies the main controller 30 of this information, and the main controller 30 instructs the cuff controller 20 to stop the air supply in step S104 in response to the notification. The cuff controller 20 keeps supplying air until it is instructed to stop the air supply. When receiving the notification of avascularization completion, the cuff controller 20 stops the pump 18.

Then, the main controller 30 starts the blood pressure measurement process. First, the main controller 30 causes the cuff controller 20 to open the constant exhaust valve 100 at a valve opening ratio corresponding to a predetermined target value (e.g., 5 mmHg/sec) of the pressure reduction ratio, and start exhausting air from the air bag 19 in the cuff 10 (S105).

The initial valve opening ratio of the constant exhaust valve 100 may also be preregistered in the cuff controller 20. In this case, the main controller 30 instructs the cuff controller 20 to start opening the constant exhaust valve 100, or notifies the cuff controller 20 of an instruction designating the initial valve opening ratio of the constant exhaust valve 100.

In either case, in accordance with the instruction from the main controller 30, the cuff controller 20 supplies an electric current corresponding to the predetermined initial valve opening ratio to the constant exhaust valve 100 through the lead 14. That is, during air supply to the cuff, the cuff controller 20 lowers the attracting force by reducing the amount of electric current supplied to set the constant exhaust valve 100 in the full closed state (FIG. 4), thereby reducing the force with which the valve membrane 270 urges the terminal portion 132 of the connector 130. This forms a gap between the valve membrane 270 and terminal portion 132, and allows the interior of the air bag 19 to communicate with the space in the case of the constant exhaust valve 100. Consequently, the high-pressure air in the air bag 19 can begin to be exhausted through the opening 150.

At the same time the constant exhaust valve 100 opens, the main controller 30 starts a blood pressure value calculating process by operating the pulse wave filter 50 and signal processor 40. An explanation of this blood pressure value calculating process will be omitted because it has no direct relation to the present invention.

The main controller 30 monitors the pressure signal 52 (S107), and determines whether the cuff pressure has fallen within the target range of target blood pressure value±allowable error calculated from the elapsed time and target pressure reduction ratio (S109).

If the cuff pressure falls within the target range, the main controller 30 determines in step S115 whether the signal processor 40 has completed the blood pressure calculating process. If the process is complete, the main controller 30 instructs the cuff controller 20 to fully open both the constant exhaust valve 100 and rapid exhaust valve 16 (S117). In response to this instruction, the cuff controller 20 stops supplying the electric current to the constant exhaust valve 100 to fully open it (FIG. 3), and also fully opens the rapid exhaust valve 16.

After that, the main controller 30 receives, where necessary, the measurement results from the signal processor 40, and displays the measurement results on the display device 60, or outputs the measurement results to another external apparatus such as a printer (not shown).

If the blood pressure calculating process is not complete in step S115, the process returns to step S107, and the main controller 30 repeats the above processing.

On the other hand, if the cuff pressure falls outside the target range in step S109, the main controller 30 adjusts the opening ratio of the constant exhaust valve 100. More specifically, if the cuff pressure is lower than the target range, the main controller 30 causes the cuff controller 20 to reduce the valve opening ratio in order to decrease the exhaust flow rate.

In step S111, the main controller 30 instructs the cuff controller 20 to reduce the exhaust flow rate. In response to this instruction, the cuff controller 20 increases the amount of electric current supplied to the constant exhaust valve 100 by a predetermined amount. The increase in amount of electric current increases the attracting force of the solenoid 200, so the core 225 attracts the valve 250. This increases the force with which the valve membrane 270 urges the terminal portion 132, and decreases the gap between the terminal portion 132 and valve membrane 270, thereby decreasing the exhaust flow rate.

Also, in step S113, the main controller 30 instructs the cuff controller 20 to increase the exhaust flow rate. In response to this instruction, the cuff controller 20 reduces the amount of electric current supplied to the constant exhaust valve 100 by a predetermined amount. The reduction in amount of electric current decreases the attracting force of the solenoid 200, and increases the distance between the valve 250 and core 225. Consequently, the force with which the valve membrane 270 urges the terminal portion 132 decreases, and the gap between the terminal portion 132 and valve membrane 270 increases. This increases the exhaust flow rate.

Note that the exhaust flow rate increases as the cuff pressure increases even at the same valve opening ratio, so it is favorable to change the degree of adjustment in accordance with the cuff pressure. For example, the main controller 30 controls the cuff controller 20 in order to decrease the valve opening ratio adjusting step when the cuff pressure is high, and increase the valve opening ratio adjusting step when the cuff pressure decreases.

In the sphygmomanometer exhaust valve of this embodiment as described above, the operation fulcrum (axis) of the valve 250 is fixed, and the valve 250 is biased. This reduces the influence of an external force such as gravity or a vibration on the amount of movement of the valve 250, and makes the attracting force of the solenoid 200 dominant. Accordingly, the valve opening ratio can be readily controlled with high reproducibility.

As many apparently widely different embodiments of the present invention can be made without departing from the spirit and scope thereof, it is to be understood that the invention is not limited to the specific embodiments thereof except as defined in the appended claims.

What is claimed is:

1. A sphygmomanometer exhaust valve characterized by comprising:
   a movable member which functions as a lever;
   a ventilation port formed in a position opposing a first portion of said movable member which functions as a point of action of said movable member thereby the point of action allows for closing and opening of said ventilation port;
   control unit adapted to control, in accordance with external control, an amount of movement of a second portion of said movable member which functions as a point of force of said movable member thereby causing movement in said movable member; and
   support unit adapted to support said movable member such that a fulcrum position of said movable member does not move, and while said control unit is preventing movement of the point of force of said movable member, said control unit holds said movable member in a predetermined position where the point of action of said movable member is spaced apart from said ventilation port,
   wherein said support unit consists of a metal plate bended such that a longitudinal cross section shape of said support unit has a bending corner, and one end of said support unit is attached to said movable member such that said bending corner functions as the fulcrum, and the other end of said support unit is fixed to a case of the sphygmomanometer exhaust valve, and
   wherein said support unit itself functions as a plate spring forcing said movable member to the predetermined position.

2. The valve according to claim 1, wherein a bending angle of said bending corner is set at an angle at which said movable member is held in the predetermined position.

3. The valve according to claim 1, wherein said movable member is made of a magnetic material, and said control unit is an electromagnet unit adapted to change an attracting force in accordance with the external control.

4. A sphygmomanometer which comprises a cuff, a pump which supplies air to said cuff, and a constant exhaust valve which exhausts said cuff, and measures blood pressure by using a pulse wave detected by said cuff and a pressure value of said cuff, wherein the sphygmomanometer exhaust valve cited in claim 1 is used as said constant exhaust valve.

* * * * *